United States Patent [19]

Attar

[11] Patent Number: 4,666,859

[45] Date of Patent: May 19, 1987

[54] REAGENT FOR COLORIMETRICALLY INDICATING THE PRESENCE OF FORMALDEHYDE

[75] Inventor: Amir J. Attar, Raleigh, N.C.

[73] Assignee: Perfect View Incorporated, Raleigh, N.C.

[21] Appl. No.: 865,042

[22] Filed: May 19, 1986

[51] Int. Cl.[4] .................... G01N 21/78; G01N 31/22
[52] U.S. Cl. .................... 436/130; 436/902; 422/57; 422/86
[58] Field of Search ............. 436/130, 128, 50, 902; 422/56, 57, 86, 87, 58; 568/448

[56] References Cited

U.S. PATENT DOCUMENTS

| | | | |
|---|---|---|---|
| 3,892,709 | 7/1975 | Oda et al. | 502/402 |
| 3,945,798 | 3/1976 | Young | 422/56 |
| 4,323,698 | 4/1982 | Haag et al. | 585/250 |
| 4,511,658 | 4/1985 | Lambert et al. | 436/130 |
| 4,552,849 | 11/1985 | Nakajama | 436/130 |

OTHER PUBLICATIONS

Merch Index 10th ed. Merck & Co. Rathway, N.J. 1983, p. 1193.

*Primary Examiner*—David L. Lacey
*Assistant Examiner*—Lori-Ann Cody
*Attorney, Agent, or Firm*—Bell, Seltzer, Park & Gibson

[57] ABSTRACT

A novel colorimetric reagent for the selective determination of formaldehyde in solution or in air is described. The reagent comprises at least two chemicals: rubeanic acid or a rubeanic acid derivative, and a cyano complex of a metal. Upon addition of formaldehyde, a color is formed which is quantitatively related to the number of formaldehyde molecules reacted. The chromophoric reagent can be mixed with other inactive ingredients such as stabilizers, buffers, polymers, etc. and used in solutions as a coating on a flat surface, or on beads to detect and determine formaldehyde colorimetrically. One particular application of the colorimetric reagent is in a direct reading colorimetric gas dosimeter for formaldehyde.

16 Claims, No Drawings

REAGENT FOR COLORIMETRICALLY INDICATING THE PRESENCE OF FORMALDEHYDE

FIELD AND BACKGROUND OF THE INVENTION

The present invention relates to a class of reagents for colorimetrically determining formaldehyde in solution or in air, and to the use of such a reagent for monitoring exposure to formaldehyde.

Formaldehyde is an important chemical which is widely used in various industries, such as plastics, textiles, etc. Because of increasing concern over safety and health hazards presented by exposure to formaldehyde vapors in air and governmental regulations limiting the permissible level of formaldehyde vapors in the workplace environment, industries require an effective and reliable way to monitor formaldehyde levels in the workplace environment and to control exposure to hazardous formaldehyde concentrations.

Various monitoring devices have been developed for monitoring exposure by individuals to formaldehyde. One popular type of monitoring device is a dosimeter badge, which is intended to be worn by persons who work in an area which may be contaminated with formaldehyde vapors. Various ways are provided for obtaining a reading of the formaldehyde exposure from the badge. However, the commercially available badges which have been developed for monitoring formaldehyde have been subject to one or more disadvantages or limitations, including expense, lack of reliability, and inability to provide a continuous direct readout of formaldehyde exposure. Many of these disadvantages and limitations are due to the chromophoric reagent used in the dosimeters.

Several reagents for colorimetric determination of formaldehyde have been described in the literature. The most important ones are described in Table 1 below.

TABLE 1

Conventional Colorimetric Reagents for the Determination of Formaldehyde

| Reagent | Comments | References* |
|---|---|---|
| Chromotropic Acid (and variations of) | Very sensitive and selective; however, it is slow and requires testing in concentrated acid. Phenol interferes in some procedures. | 1-2 |
| Schiff's Reagent | Very sensitive and reasonably selective. Utilizes cumbersome reagents. The color formed is not stable. The reagents are not stable. | 3 and references therein, 4-5 |
| MBTH (3-methyl-2-benzothiazolone hydrazone) | Very sensitive reagent for ketones and aldehydes, (but is not selective to formaldehyde. The reagent is unstable. Used mainly for TOTAL aldehydes in air. | 6-7 |
| Potassium ferricyanide phenylhydrazine. | Very sensitive and reasonably selective; The reagent is, however, very unstable. | 8 |
| Silver chromate-ethylene diamine | Reasonably sensitive. However, the reagent is unstable and can be used only in non-acidic solutions. | 9 |
| Nickel cyanide and dimethyl glyoxime. | Sensitive and reasonably selective; however, it takes a long time to develop the full color. | 10 |

*References
1. Taylor, D. G. (Manual Coordinator), "NIOSH Manual of Analytical Methods," Vol. I, Section 125 (1977).
2. Knox, S. E. and Hee, S. Q., Am. Ind. Hyg. Assoc., 45 (5), 325-328 (1984).
3. Walker, J. F., "Formaldehyde," Chapt. 20, 3rd Ed., ACS, New York, 1964.
4. Miksch, R. R., Anthon, D. W., Fanning, L. Z., Hollowell, C. D., Revzan, K. and Glanville, J., Anal. Chem., 53, 2118-2123 (1981).
5. Kuijpers, A. T. J. M. and Neele, J., Anal. Chem., 55, 390-391 (1983).
6. Miksch, R. R. and Anthon, D. W., Am. Ind. Hyg. Assoc. J., 43, 362-365 (1982).
7. Katz, M. (ed.), "Methods of Air Sampling and Analysis," APHA Intersociety Committee, 2nd Ed., Am. Pub. Health Assoc., Washington, D.C. 20036 (1977).
8. Schrvver, S. B., Pres. Roy. Soc. London (B), 82, 226 (1910).
9. Neto c. Chem. Abst. 54, 1160 (1960).
10. West, T. W. and Sen, B., Anal. Chem., 27, 1460 (1955).

However, the above-noted known colorimetric reagents all suffer from at least one of the following disadvantages:

1. They form color very slowly.
2. The reagents are unstable.
3. The reagents cannot be easily used in the field.
4. The reagents cannot be adapted to dry-chemistry application.
5. The reagents are non-selective to formaldehyde.

The present invention provides a colorimetric reagent which can visibly show the presence of formaldehyde, and which is useful in various applications, such as for example in a direct reading colorimetric gas dosimeter. The availability of a colorimetric reagent which can visibly show the presence of formaldehyde can help even unskilled personnel determine whether they are present in a dangerous environment.

SUMMARY OF THE INVENTION

The present invention is based upon a colorimetric reaction involving two chemicals: rubeanic acid (dithiooxamide) or a derivative thereof and a metal-cyanide complex, preferably a cyano complex of a metal selected from the group consisting of silver, copper, cadmium, lead, iron, bismuth, cobalt, thallium, nickel, gold, palladium, platinum, and ruthenium.

The essence of the colorimetric reaction is the formation of colored compounds due to the reaction between a metallic ion and rubeanic acid or a derivative of rubeanic acid. If sufficient cyanide ions are present, a metal-cyanide complex is formed which does not form color. However, when formaldehyde is added to a solution which contains the metal-cyanide complex, the cyanide ion reacts with the formaldehyde according to the reaction:

$$CH_2O + CN^- \rightarrow CH_2CNO^-$$

which destroys the complex and releases metallic ions. The metallic ions, in turn react with the rubeanic acid or rubeanic acid derivative and form color. The degree of color change is quantitatively related to the number of formaldehyde molecules reacted.

The colors formed with different metal complexes are: Ag—yellow-brown to black; Bi—yellow-brown to black; Pb—yellow; Cu—green-black; Cd—yellow; Fe (II)—blue; Co (II)—brown to orange-yellow; Ni (II)—blue-violet; Pd—orange-yellow to red; Au—orange; Ru (III and IV)—blue; Pt—rose-red; Tl—yellow.

The colorimetric reaction may effectively employ either rubeanic acid (dithiooxamide) or derivatives of rubeanic acid in which one or both of the hydrogen atoms of one or both of the amino groups is replaced with other organic moieties, such as for example alkyls (e.g. methyl, ethyl, hydroxyalkyls, aryls (e.g. benzyl, halobenzyl, pyridyl).

The concentration and relative proportions of the rubeanic acid and the metal-cyanide complex in the reagent are not critical, and may be varied over a wide range depending upon the sensitivity desired.

The reagent composition is preferably maintained, typically in excess of pH 10.5, by including in the reagent composition suitable bases or alkaline compounds, such as alkali metal cyanides for example.

Various additives may be included in the reagent in addition to the rubeanic acid and metal-cyanide complex, such as for example, a buffer—typically a borate, a stabilizer, an electrolyte, a solvating media, a gelling media, and polymers or prepolymers such as polyvinyl alcohol, polyvinylidene ethylene oxide, polyethylene glycol, polyvinyl acetate and functionalized polystyrene.

The reagent may be used for detecting the presence of formaldehyde in a gas mixture such as air or in an aqueous solution. The reagent may be used in the form of a solution or it may be dried on a suitable carrier or substrate.

EXAMPLE 1

An exemplary formulation of chromophoric reagent for the detection of traces of formaldehyde in solution is as follows:
1. $KAg(CN)_2$: 20 ml. of 0.75 molar in $H_2O$.
2. KCN: 1 gm.
3. Rubeanic acid: 20 ml. Sat. solution in $CH_3OH$ at 21° C.
4. $KNO_3$: 1.5 gm.
5. $KBO_3$: 0.7 gm.
6. water: as solvent for the $KAg(CN)_2$
7. methanol: 100 ml.

EXAMPLE 2

An exemplary formulation of the chromophoric reagent for the detection of traces of formaldehyde in air is as follows:
1. $KAg(CN)_2$: 20 ml. of 0.75 molar in $H_2O$
2. KCN: 1 gm.
3. Rubeanic acid: 20 ml. Sat. solution in $CH_3OH$ at 21° C.
4. $KNO_3$: 1.5 gm.
5. $KBO_3$: 0.7 gm.
6. glycerol: 10 gm.
7. polyethylene glycol: 10 gm.
8. polyvinyl alcohol: 5 gm.
9. water: as solvent for the $KAg(CN)_2$
10. methanol: 100 ml.

EXAMPLE 3

The reagent of Example 2 is used in a dosimeter badge for detection of formaldehyde by applying drops of the reagent to a carrier media, such as filter paper or a granular sorbent material such as silica or alumina, and allowing the reagent to dry. The chromophore-treated carrier is then encapsulated in a case formed of a gas impermeable plastic material having an opening formed therein to allow the ambient gas to enter the case and contact the carrier. Preferably, a permeable membrane is disposed between the opening and the carrier to reduce the effect of wind superfacial velocity on the reading. Upon exposure to formaldehyde vapors, the chromophore-treated carrier changes color, forming a yellow to brown-black color which is quantitatively related to the number of formaldehyde molecules reacted.

EXAMPLES 4 AND 5

A chromophoric reagent is produced with the formulation as set forth in Examples 1 and 2, but substituting for ingredient #3 (Rubeanic Acid) 20 ml. of N,N' Bis(2-hydroxy-ethyldithiooxamide) at a concentration of 0.08 molar.

That which is claimed is:

1. A chromophoric reagent for colorimetrically indicating the presence of formaldehyde comprising rubeanic acid or a derivative of rubeanic acid and a metal-cyanide complex being present in an amount effective to produce a color change in the presence of formaldehyde.

2. A chromophoric reagent according to claim 1 in the form of a solution of said rubeanic acid and said metal-cyanide complex in a solvent.

3. A chromophoric reagent according to claim 1 wherein said rubeanic acid and said metal-cyanide complex are in the form of a dried coating on a substrate.

4. A chromophoric reagent according to claim 1 wherein said metal-cyanide complex comprises a cyano complex of a metal selected from the group consisting of silver, copper, cadmium, lead, iron, bismuth, cobalt, thallium, nickel, gold, palladium, platinum and ruthenium.

5. A chromophoric reagent according to claim 1 wherein said rubeanic acid or said derivative, is a compound selected from the group consisting of N,N' dialkyl rubeanic acid, N,N' dihydroxyalkyl rubeanic acid, and N,N' diarylrubeanic acid.

6. A chromophoric reagent according to claim 1 wherein said metal-cyanide complex comprises potassium silver cyanide.

7. A chromophoric reagent for colorimetrically indicating the presence of formaldehyde comprising rubeanic acid or a derivative of rubeanic acid, potassium silver cyanide and, potassium cyanide, being present in an amount effective to produce a color change in the presence of formaldehydre, said reagent further comprising potassium nitrate and potassium borate.

8. In a gas dosimeter including a reagent for colorimetrically indicating the presence of formaldehyde, the improvement wherein said reagent comprises an effective amount of rubeanic acid or a derivative of rubeanic acid and an effective concentration of metal-cyanide complex.

9. A gas dosimeter according to claim 8 wherein said metal-cyanide complex comprises a cyano complex of a metal selected from the group consisting of silver, copper, cadmium, lead, iron, bismuth, cobalt, thallium, nickel, gold, palladium, platinum, and ruthenium.

10. A gas dosimeter according to claim 8 wherein said metal-cyanide complex comprises potassium silver cyanide.

11. A gas dosimeter for colorimetrically indicating the presence of formaldehyde, said dosimeter comprising a housing having an opening therein through which ambient gas may pass, a carrier layer disposed within said housing, and a chromophoric reagent which changes color in response to exposure to formaldehyde carried by said carrier, said chromophoric reagent comprising an effective amount of rubeanic acid or a rubeanic acid derivative and an effective concentration of metal-cyanide complex.

12. A method for colorimetrically indicating the presence of formaldehyde which comprises a fluid containing formaldehyde exposing a chromophoric reagent comprising an effective amount of rubeanic acid or a rubeanic acid derivative and an effective concentration of a metal-cyanide complex, and observing the change in color of said reagent.

13. A method according to claim 12 wherein said fluid is formaldehyde vapors.

14. A method according to claim 12 wherein said fluid is an aqueous solution of formaldehyde.

15. A method according to claim 12 wherein said metal-cyanide complex comprises a cyano complex of a metal selected from the group consisting of silver, copper, cadmium, lead, iron, bismuth, cobalt, thallium, nickel, gold, palladium, platinum, and ruthenium.

16. A method according to claim 15 wherein said metal-cyanide complex comprises potassium silver cyanide.

* * * * *

UNITED STATES PATENT AND TRADEMARK OFFICE
CERTIFICATE OF CORRECTION

PATENT NO. : 4,666,859

DATED : May 19, 1987

INVENTOR(S) : Amir J. Attar

It is certified that error appears in the above-identified patent and that said Letters Patent is hereby corrected as shown below:

Column 4, Line 48, "formaldehydre" should be -- formaldehyde --.

Column 5, Claim 12 should read as follows:

A method for colorimetrically indicating the presence of formaldehyde which comprises exposing a fluid containing formaldehyde to a chromophoric reagent comprising an effective amount of rubeanic acid or a rubeanic acid derivative and an effective concentration of metal-cyanide complex, and observing the change in color of said reagent.

Signed and Sealed this

Twenty-third Day of February, 1988

Attest:

DONALD J. QUIGG

*Attesting Officer*   *Commissioner of Patents and Trademarks*